| United States Patent [19] | [11] Patent Number: 4,997,915 |
| --- | --- |
| Tan et al. | [45] Date of Patent: Mar. 5, 1991 |

[54] PURIFICATION OF PERTUSSIS TOXINS

[75] Inventors: Larry U. L. Tan, Mississauga; Dirk Alkema, Stayner; Gail Jackson, Richmond Hill; Po S. Wah, Willowdale; Raafat E.F. Fahim, Mississauga, all of Canada

[73] Assignee: Connaught Laboratories Limited, Willowdale, Canada

[21] Appl. No.: 333,964

[22] Filed: Apr. 6, 1989

[30] Foreign Application Priority Data

Apr. 5, 1988 [GB] United Kingdom ............... 8807860

[51] Int. Cl.$^5$ .................... A61K 39/02; A61K 39/10; C07K 3/18; C07K 3/12
[52] U.S. Cl. .................................. 530/396; 424/92; 435/71.2; 530/380
[58] Field of Search ................. 424/92; 530/380, 396; 435/71.2

[56] References Cited

U.S. PATENT DOCUMENTS

| 4,455,297 | 6/1984 | Syukuda et al. | 424/92 |
| 4,563,303 | 1/1986 | Ginnaga et al. | 530/417 |
| 4,687,738 | 8/1987 | Ginnaga et al. | 435/71.2 |
| 4,705,686 | 11/1987 | Scott et al. | 424/92 |
| 4,784,589 | 11/1988 | Robinson et al. | 424/92 |

*Primary Examiner*—Howard E. Schain
*Assistant Examiner*—Choon P. Koh
*Attorney, Agent, or Firm*—Sim & McBurney

[57] ABSTRACT

Lymphocytosis promoting factor (LPF) and filamentous hemaglutinin (FHA) are isolated from the growth medium of the *Bordatella pertussis* organism and purified by selecting adsorbing the LPF and FHA on a selective adsorbing medium, such as filter aids or gel filtration media, at low ionic strength and subsequently removing the adsorbed LPF and FHA at using an aqueous medium of high ionic strength, either simultaneously or sequentially. Prior to desorbtion of the LPF and FHA, the adsorbing medium may be contacted with an aqueous solution of a non-ionic detergent, which enables the LPF and FHA subsequently desorbed to be substantially free from contamination by lipopolysaccharides (LPS). The LPF and FHA may be further purified on hydroxyapatite. The LPF and FHA may be detoxified separately or together by contacting with a cross-linking agent, such as glutaraldehyde or formaldehyde, in the presence of an anti-aggregation agent. The resulting purified and detoxified LPF and FHA may be used to formulate a vaccine against pertussis.

19 Claims, No Drawings

PURIFICATION OF PERTUSSIS TOXINS

FIELD OF INVENTION

The present invention relates to a novel method of isolation and purification of specific proteins from the fermentation broth of the organism *Bordatella pertussis*, the removal of pyrogenic factors from these proteins, the detoxification of the proteins and the preparation from these purified proteins of a vaccine that is virtually non-toxic, has little or no side effects and confers protection against the disease of pertussis.

BACKGROUND OF THE INVENTION

For infants below the age of 24 months, the disease caused by *Bordatella pertussis*, pertussis or whooping cough, can be very severe and has a mortality rate of approximately 1%. Over the last fifty years, three types of vaccine have been available for immunization against the disease. The most widely used vaccine, that has been available for the protection of infants against pertussis infection, in combination with tetanus and diphtheria vaccines, is the so-called "whole cell" vaccine, which is available in all developed countries, and many of the Third World countries.

This whole cell pertussis vaccine is prepared by growing known strains of the *B.pertussis* organism in a defined medium for several hours in a fermentor, until the mixture reaches certain defined parameters. The mixture then is treated with a chemical agent, such as formaldehyde, which kills the organism and detoxifies proteins present in the supernatant and in the organism itself. After allowing the mixture to stand for a specified time to ensure that this detoxification procedure is complete, the cells are separated from the supernatant by passing the mixture through a continuous centrifuge, to provide a packed mass of cells and the supernatant, which is discarded. The cells then are resuspended in a solution of sodium chloride to provide a suspension, that, when diluted to a known strength, usually determined by the opacity of the suspension, and injected subcutaneously, elicits antibodies that are protective against the disease. This "whole cell" vaccine is known for giving minor local reactions at the injection site with occasionally more severe overall reactions, such as elevated temperature and general fretfulness. There has been speculation that the vaccine is responsible for some neurological reactions in infants.

In a second vaccine type, the *B.pertussis* was grown and detoxified with formaldehyde as before, and then the isolated cells extracted with a concentrated solution of urea. After filtration and dialysis to remove the urea, a mixture of soluble cell wall components is obtained, which, after dilution to a known strength, was in use as a vaccine from 1969 to 1974, but has now been withdrawn because of poor efficacy. More recently, a third vaccine type, commonly called an acellular vaccine, that is in use in Japan and is in clinical trials in a number of other developed countries, is prepared by isolation and purification of constituents of the culture supernatants of *B.pertussis* after detoxification. Specifically, the constituents called lymphocytosis promoting factor (LPF) also known as pertussis toxin (PT), filamentous hemaglutinin (FHA) and agglutinogens have been isolated and identified. However, because of variations in growth of the organism and the method of isolation, which is non-specific, the composition of the isolated mixture of proteins can vary. At present there is no vaccine in general use and licensed that is completely non-toxic and still gives good protection.

With the growth of the science of immunology over the years, it has been recognized that protective antibodies against a specific disease can be elicited by the administration of specific cellular components of the organism that causes the disease, rather than the whole organism that has been inactivated or has been attenuated to give a non-pathogenic strain. It has been recognized that use of detoxified or attenuated organisms as a vaccine can introduce components that may be damaging to the recipient. With this in mind, a number of efforts have been made to isolate components of the pertussis organism, either from the cell or that have been excreted into the medium, that could have antigenic capabilities, be completely non-toxic and thus could act as vaccines.

As yet there has been no convincing proof that any one particular cell component, by itself, can act as a protective antigen. However, in a number of publications and Patent applications (see, for instance, European Patent Application Nos. 0231083 and 0175841) it has been suggested that a mixture of the purified and detoxified proteins, lymphocytosis promoting factor (LPF) and filamentous hemaglutinin (FHA), can act as a combined antigen and, when administered to a mammal, generate antibodies that confer protection against the disease. In the aforesaid publications various methods have been disclosed for obtaining these proteins in a purified form, and once purified using them in varying proportions as a vaccine.

Although existing technology produces highly purified LPF and FHA, the processes have inherent drawbacks. The affinity chromatographic methods that have been used are effective but conditions of absorption and elution often use materials which are toxic, expensive and/or denature the required proteins. In addition, some of the materials used on affinity columns can be leached into the product under the harsh elution conditions required and, since some of the leached materials are blood derived, may introduce the possibility of blood born diseases or autosensitization. The use of gel filtration materials and hydroxyapatite are acceptable when used by themselves, but give only low purification factors.

The LPF and FHA, which are produced by *B.pertussis*, also represent a major challenge in the removal of lipopolysaccharides (LPS) as a contaminant. LPS even in nanogram quantities can produce fever and are an undesirable component of any vaccine. The initial concentration of LPS in the fermentation supernatant can be as high as one milligram per milliliter. A number of methods have been used to remove pyrogens from vaccines (see, for instance, U.S. Pat. Nos. 4,000,257 and 4,380,511). Many of these methods are too harsh and result in denaturation of the required proteins. Other methods are ineffective, cumbersome to use and expensive.

Before using the LPF and FHA in a vaccine, these proteins must be detoxified since the LPF in its natural state is highly toxic and small amounts are still present in the purified FHA. This process previously has been achieved by treating the proteins with a chemical agent which induces cross-linking. Traditionally, the agents used have been formaldehyde and glutaraldehyde. The use of formaldehyde and glutaraldehyde can lead to heavy losses due to aggregation and precipitation.

SUMMARY OF INVENTION

In accordance with the present invention, there is provided a novel method for the isolation and purification of the proteinaceous materials LPF and FHA from the growth medium of B.pertussis by adsorption and desorption on various substrates, using a combination of low and high ionic strength solutions. In addition, there is provided an improved method of removing pyrogenic factors, as exemplified by LPS, from the LPF and FHA by washing the adsorbed proteins with a detergent solution. Further, there is provided an improved method for the detoxification of the LPF and FHA, using a cross-linking agent in the presence of an anti-aggregation agent, such that the purified materials can be readily combined into an efficacious vaccine for the prevention of the disease of pertussis.

Accordingly, in one aspect of the present invention, there is provided a method for the isolation and purification of the proteinaceous materials called lymphocytosis promoting factor (LPF) and filamentous hemaglutinin (FHA) from a growth medium in which has been grown the Bordatella pertussis organism. The method comprises contacting the growth medium at low ionic strength with a solid particulate adsorbing medium to selectively adsorb LPF and FHA from the growth medium, and sequentially or simultaneously desorbing the proteinaceous materials by contacting the adsorbing medium with an aqueous medium of high ionic strength.

The isolated LPF and FHA, after further purification and detoxification, can be formulated into a non-toxic vaccine for protection against pertussis.

GENERAL DESCRIPTION OF INVENTION

The inventors have determined that LPF and FHA can be adsorbed preferentially from the filtered growth medium of B.pertussis, at low ionic strength, onto a variety of solid particulate adsorbent materials. After the LPF and FHA are adsorbed from the growth supernatant at low ionic strength onto the substrates, they are desorbed from the adsorbent material using an aqueous solution of high ionic strength.

The high ionic strength desorbing medium is an aqueous solution of a salt and/or buffer. The term "salt solution" used herein refers to all metal or ammonium salts, such as potassium nitrate, sodium chloride and ammonium sulfate, which when dissolved in water, dissociate into their constituent ions, thereby increasing the ionic strength of the solution without significantly changing the pH of the solution. The term "buffer" used herein refers to a chemical compound which, when dissolved in water, dissociates into their constituent ions, thereby increasing the ionic strength of the solution and having buffering capacity.

As used herein, the term "low ionic strength", refers to an aqueous medium having a conductivity of about 11 mS/cm or less, preferably about 4 mS/cm. The unit of measurement mS/cm is millisiemen per centimeter. A siemen (S) is a unit of conductivity and is the equivalent of the inverse of resistance (ohm) and is sometimes designated mho. The term "high ionic strength" as used herein refers to an aqueous medium having a conductivity of greater than about 11 mS/cm and preferably at least about 50 mS/cm.

Solid particulate adsorbent materials useful in the present invention include filter aids, such as Perlite (which is of volcanic ash origin) and Celite (a diatomaceous earth), siliceous materials, such as sand, celluloses, agaroses and gel filtration materials, such as the Sepharoses, the Sephadexes, ultragel and their derivatives.

The variety of matrix materials which have been found useful for the adsorbing medium in the present invention suggests that the characteristics of the matrix material are non-critical but rather it is the property of LPF and FHA that, under low ionic strength conditions, they will bind to a large variety of matrices.

While not wishing to be found by any particular theory to explain the process of the invention, it is thought that, under the initial low ionic strength conditions employed, the LPF and FHA are close to coming out of solution. By passing the solution in contact with insoluble particulate matrices, the particles of the matrix act as nuclei onto which the LPF and FHA can precipitate. Resolubilization for desorbtion then requires a higher ionic strength solution.

After desorption from the absorbing medium by the high ionic strength solution, a mixture of the two proteins is obtained, that can be further separated on other materials, such as hydroxyapatite or other ion-exchange resins, to give the two proteins in high yields and high purity. Alternatively, we have found that separation of FHA and LPF after adsorption onto the adsorbing medium can be obtained by desorbing from the adsorbing medium at differing ionic strengths. To effect preferential elution of LPF from the adsorbing medium, an ionic strength of solution of about 11 mS/cm to about 20 mS/cm is employed. Once the LPF has been eluted, FHA can be eluted at an ionic strength of solution of at least 20 mS/cm, preferably at least about 50 mS/cm.

The ability to effect adsorption at low ionic strength and subsequent elution at high ionic strength of LPF and FHA on conventional gel filtration media and the other non-derivatized adsorbing media used herein is totally unexpected and deviates from the state of the art, where proteins are not adsorbed to gel filtration media and where the protein is continuously eluted from the column under isocratic, i.e., a single buffer, conditions. The gel media have been chosen in previous work because of their very low non-specific protein adsorption, and yet, under the conditions of the invention, they will still adsorb the LPF and FHA very well. It has been shown by the inventors that FHA and LPF can be purified to a greater degree on agarose than derivatized agarose.

The method can be used either as a batch process on the cell free media obtained from the growth of the organism or as a separation method on a chromatography column of the adsorbent. Because of their ease of filtration, their low costs and the accepted employment of filter-aids in the manufacture of pharmaceutical products, the use of the filter-aids is preferable to the use of other materials, such as gel filtration media, and derivatized materials.

The inventors have further found that, if the proteins adsorbed onto the matrices are washed, before elution, with an aqueous non-ionic detergent solution, the LPS in the final product can be reduced by a factor of 10,000 to 100,000, to a concentration of about 1 to about 10 ng/mL. Examples of suitable non-ionic detergent solutions are Triton X-100 in a concentration of about 0.005 to about 5% (v/v), preferably about 0.1 to about 1% (v/v), and Nonidet p40 in a concentration of about 0.0005 to about 0.1% (v/v), preferably about 0.001 to about 0.01% (v/v).

It has also been found by the inventors that the purified LPF and FHA can be detoxified by contact with a cross-linking agent, such as glutaraldehyde and/or formaldehyde in the presence of an anti-aggregation agent, such as glycerol or sucrose, to improve the yield of final product. The anti-aggregation agent is present in a significant proportion during the detoxification operation and prevents the aggregation and precipitation that occurs in the absence of such material. For the detoxification of LPF in the presence of glycerol, glycerol is present in an amount of about 30 to about 80% (v/v), preferably approximately 50%, while for the detoxification of FHA, glycerol is present in an amount of about 10 to about 80% (v/v), preferably approximately 25%. Where sucrose is used as the anti-aggregation agent, the sucrose is present in an amount of about 30 to about 60% (w/v), preferably approximately 40%.

In the present invention, B.pertussis is grown in a fermentor using controlled conditions. Carbon sources and growth factors are supplemented continuously or in batches at various intervals during the fermentation until the two proteins, LPF and FHA, are at the desired level, which can be determined by enzyme linked immunosorbent assay (ELISA). In our invention, the mixture of cells and medium from the fermentor is not inactivated by chemical means immediately after the fermentation is complete, but later in the purification process. The use of chemical detoxification at this stage in the process can lead to aggregation of the proteins and poor separation in the following steps.

The fermentor then is harvested and the majority of the cells removed by continuous centrifugation. The remainder of the cells then can be removed from the supernatant by filtration, using known membrane filters of 0.2 μ pore size, which also sterilizes the solution. In the present invention, it is this supernatant that is retained and processed for isolation and purification of LPF and FHA. After centrifugation and filtration, the supernatant is concentrated, say 10-fold, using membrane filtration, assayed for protein and then diluted until the ionic strength is in the required range. This solution, which contains the LPF and FHA proteins then is treated with the adsorbing medium, either in a batch process or as a chromatographic process. The LPF and FHA, after adsorption onto the adsorbing medium, are washed first with several volumes of a buffer to remove contaminants and then with a solution of a detergent which removes the majority of the lipopolysaccharides (LPS). Further washing removes any traces of the detergent.

The LPF and FHA can be obtained separately from the adsorbent by elution with solutions of stepwise increasing ionic strength or the two proteins can be eluted together using a high ionic strength salt solution. The proteins can be further purified on a chromatography column of a material, such as hydroxyapatite. The proteins are eluted from such a column by using different ionic strengths solutions after prior washing. The separate proteins then are detoxified in the presence of an anti-aggregation agent to result in high yields of detoxified protein. After removal of the additives, the detoxified proteins are sterilized by filtration and, after assay, can be mixed in the required proportion to give a solution that can be used as a vaccine against pertussis.

DESCRIPTION OF PREFERRED EMBODIMENT

The procedure of the invention may be employed to effect large scale separation of LPF and FHA using a chromatographic column of Perlite, which is currently the best mode known to the applicants for effecting separation and recovery of purified LPF and FHA.

Concentrated *B.pertussis* fermentation broth is diluted to a low ionic strength corresponding to a conductivity of 4mS or less and loaded onto a column of packed Perlite to provide a protein loading of about 1 to about 5 mg, preferably about 2 to about 3 mg per milliliter of packed Perlite. The packed Perlite column usually about 15 to about 18 cm high and about 10 to about 45 cm in diameter.

The dilute fermentation broth is contacted with the Perlite column at a linear flow rate of about 50 to about 200 cm/hr, preferably approximately 100 cm/hr. The proteins which are adsorbed to the Perlite are almost exclusively LPF and FHA with most of the contaminating proteins and LPS passing through the column.

The column then is washed with about 2 to about 10 column volumes of a buffer containing about 10 to about 50 mM, of Tris HCl at pH 8.0. A subsequent wash with an aqueous non-ionic detergent, typically about 5 column volumes of an 0.5% (v/v) Triton X-100 solution in 50 mM Tris HCl buffer at pH 8.0, decreases the LPS content of the proteins by a factor or about 100, for a total decrease in the LPS/LPF ratio of between 10,000 and 100,000. Subsequent washing of the column with further volumes preferably about 5 volumes of buffer, of 50 mM Tris HCl at pH 8.0, removes the non-ionic detergent.

The FHA is eluted from the column by contacting the column with buffer solution, for example, 5 volumes of 50 mM Tris HCl at pH 8.0, containing about 0.1 to about 0.2 mM sodium chloride, preferably about 0.12 mM. The LPF next is eluted from the column by contacting the column with buffer solution, for example, 5 volumes of 50 mM Tris HCl at pH 8.0, containing at least about 0.2M of sodium chloride, preferably about 0.6M.

The eluted solutions are assayed for protein content. By this procedure, LPF and FHA recoveries of approximately 60 to 65% and 65 to 70% respectively of the initial contents of these proteins in the broth have been obtained.

Further purification of LPF and FHA may be effected using a column of packed hydroxyapatite about 5 to about 8 cm in height and about 5 to about 30 cm in diameter. The column is washed and equilibrated prior to use. The eluate containing LPF is applied to the column at a loading of about 0.5 to about 1 mg/ml of packed gel at a linear flow rate of about 15 to about 25 cm/hr to adsorb the LPF therefrom.

The column is washed with a suitable buffer, for example, 5 column volumes of 30 mM potassium phosphate at pH 8.0, following which the LPF is eluted with about 5 to about 10 column volumes of an eluting medium, for example, 75 mM potassium phosphate at pH 8.0, containing about 0.1 to about 0.3M sodium chloride, preferably about 0.225M.

The procedure may be repeated for the FHA-containing eluant, with elution being effected using an aqueous elution medium, for example, 200 mM potassium phosphate at pH 8.0, containing at least about 0.2M sodium chloride, preferably about 0.6M.

In these hydroxyapatite purification procedures, typical recoveries of the pure protein are about 80 to about 100% with the respective proteins having a purity of at least 90%.

Detoxification of the further purified LPF and FHA may be effected in order to provide these materials in a form suitable for formulation as a non-toxic vaccine. It is preferred to effect detoxification of the LPF protein using glutaraldehyde in the presence of glycerol while it is preferred to effect detoxification of the FHA protein using formaldehyde in the presence of glycerol.

The invention is illustrated further by the following Examples.

EXAMPLES

Methods of protein biochemistry, fermentation and assays used but not explicitly described in this disclosure and these Examples are amply reported in the scientific literature and are well within those skilled in the art.

Example 1

This Example illustrates the growth of B.pertussis in fermentors.

Bordatella pertussis was seeded into a fermentor containing 250 L of broth (modified Stainer-Scholte medium). During the period of perfentation, monosodium glutamate (2.18 kg) and the growth factors, glutathione (41 g), ferrous sulphate (2.7 g), calcium chloride (5.5 g), ascorbic acid (109 g), niacin (1.1 g) and cysteine (10.9 g), were added at intervals to increase the yields of LPF. At the end of a 48 hour fermentation period, the broth was run through a continuous centrifuge to remove the majority of the cells. This suspension, which contains both the LPF and FHA in solution, was further clarified by micro-filtration on cellulose acetate membranes (0.22 μm pore size). The sterilized filtrate was concentrated approximately 10-fold using a 20,000 NML membrane and then assayed for protein by the dye-binding method.

Example 2

This Example illustrates the isolation of LPF and FHA on a number of different matrices.

A number of 1 milliliter columns were packed with various matrices and equilibrated with 50 mM Tris HCl at pH 8.0, 10 mM potassium phosphate at pH 8.0 or water. The matrices included Orange A-, Blue A-, Green A-, Red A-agaroses, Blue Sepharose, Blue B-, Reactive Blue 4-, Cibacron Blue 3GA-, Reactive Brown 10-, Reactive Green 19-, Reactive Yellow 86-Sepharose, non-derivatized agarose, Ultragel ACA44, Sephadex G50, Sepharose 6B, Sepharose CL4B, S-Sepharose, Q-Sepharose, cellulose sulphate, QAE-cellulose, CM-cellulose, Perlite and Celite.

B. pertussis culture broth was centrifuged, sterile filtered through a 0.2 u membrane and concentrated approximately 10 fold by ultrafiltration on 20 kD NML membranes. Broth concentrates were diluted with water so that the ionic strength was less than or equal to 4 mS/cm. Samples between 2 to 10 ml were loaded onto the columns by gravity feed and then washed with excess 10 mM potassium phosphate, followed by 50 mM Tris HCl buffer at pH 8.0. Each column was eluted with 50 mM Tris HCl at pH 8.0 containing either 0.6M or 1.0M sodium chloride. Fractions were analysed by absorbance at 280 nm and on SDS-PAGE. All of the matrices were found to adsorb LPF and FHA. The eluted LPF and FHA were found to be highly purified.

In a similar experiment using white quartz sand, a column 1.5 cm in diameter and 18 cm in height was washed and loaded with the same diluted broth concentrate to adsorb LPF and FHA therefrom and washed. The column then was eluted first with 50 mM Tris HCl at pH 8.0 containing 0.1M sodium chloride, followed by Tris buffer containing 1.0M sodium chloride, so as to elute first the LPF and then the FHA. The separately eluted LPF and FHA respectively were found to be highly purified.

Example 3

This Example illustrates the large scale separation of LPF and FHA using a chromatographic column of Perlite.

The broth concentrate, prepared as described in Example 1, was diluted with water to a conductivity of approximately 4 mS/cm, such that the final loading of protein was approximately 3 mg of crude protein per milliliter of packed Perlite. The packed Perlite column was 18 cm high and 10 cm in diameter and was prewashed with 1.4 L of Water for Injection (WFI). The diluted concentrate was applied to the column at a linear flow rate of 100 cm/hr. The proteins bound to the Perlite were almost exclusively LPF and FHA with most of the contaminating protein and lipopolysaccharide (LPS) passing through. The column was washed with 1.4 L of a buffer containing 50 mM Tris HCl at pH 8.0. A subsequent wash with detergent, composed of 1.4 L of a 0.5% (v/v) Triton X-100 solution in 50 mM Tris HCl buffer at pH 8.0, reduced the LPS content by a further factor of 100, for a total reduction in the LPS/LPF ratio of between 10,000 to 100,000. The column then was washed with a further 1.4 L 50 mM Tris HCl at pH 8.0 to remove the Triton X-100. The LPF then was eluted from the column with 50 mM Tris HCl at pH 8.0 containing 0.12 mM sodium chloride. The FHA was eluted from the column using 50 mM Tris HCl at pH 8.0 containing 0.6M sodium chloride. Approximately 1.4 L of each elution buffer was used. The solutions then were assayed for protein content by the dye-binding assay. LPF and FHA recoveries were 60% and 65%, respectively, based on ELISA values.

Example 4

This Example illustrates the batch adsorption of LPF and FHA on Perlite.

B.pertussis broth concentrates (60 ml) were diluted 4-fold with water to a conductivity of approximately 4 mS/cm and Perlite (2g) added. The mixture was rotated slowly at 4° C. for 3 hr. The mixture was vacuum filtered on a sintered glass filter and the residual Perlite was rinsed into the filter with 50 mM Tris HCl at pH 8.0 (20 ml). The Perlite was washed with 4×50 ml of the Tris buffer and then eluted with 3×20 ml of 50 mM Tris HCl at pH 8.0 containing 1.0M sodium chloride. The eluates were pooled and assayed using an ELISA assay. LPF recoveries were calculated to be at least 65%.

EXAMPLE 5

This Example illustrates the further purification of LPF on hydroxyapatite.

Hydroxyapatite was packed into a column 5 to 30 cm diameter and 6 cm height. The column was washed with 200 mM potassium phosphate at pH 8.0, 1M potassium chloride, 0.5% Triton X-100 and equilibrated with 10 mM potassium phosphate at pH 8.0 prior to use. The LPF solution, recovered as described in Example 3, was applied to the column at a loading of approximately 0.5 mg of protein/ml of packed gel at a linear flow rate of approximately 20 cm/hr. The column was washed with 500 ml of 30 mM potassium phosphate at pH 8.0. The LPF was eluted with 1 L of 75 mM potassium phosphate at pH 8.0 containing 0.225M sodium chloride. The resulting LPF was at least 90% pure. The LPF was assayed for protein by the dye binding method. The LPF recovery was approximately 90% for this step.

Example 6

This Example illustrates the further purification of FHA on hydroxyapatite.

The hydroxyapatite was packed and washed in a column of the same size as detailed in Example 5. The FHA fraction from the Perlite separation described in Example 3 was applied to the column at a linear flow rate of 20 cm/hr and a loading of 0.5 mg of protein/ml of packed gel. The column was washed with 500 ml each of 30 mM potassium phosphate at pH 8.0, 30 mM potassium phosphate at pH 8.0 containing 0.5% (v/v) of Triton X-100 and 30 mM potassium phosphate at pH 8.0. Any remaining LPF in the fraction first was eluted with 500 ml of 85 mM potassium phosphate at pH 8.0 and the FHA then was eluted with 200 mM potassium phosphate at pH 8.0 containing 0.6M potassium chloride. The resulting FHA was at least 90% pure. The FHA was assayed for protein by the Lowry method. FHA recovery for this column was approximately 90%.

Example 7

This Example illustrates the detoxification of LPF with glutaraldehyde.

The purified LPF, prepared as described in Example 5, in 75 mM potassium phosphate at pH 8.0 containing 0.22M sodium chloride was diluted with an equal volume of glycerol to a protein concentration of approximately 200 μg/ml. The solution was heated to 37° C. and detoxified by the addition of glutaraldehyde to a final concentration of 0.5% (w/v). The mixture was kept at 37° C. for 4 hr and followed by the addition of aspartic acid (1.5M) to a final concentration of 0.25M. The mixture was incubated at room temperature for 1 and then diafiltered with 10 volumes of 10 mM potassium phosphate at pH 8.0 containing 0.15M sodium chloride to remove both the glycerol and the glutaraldehyde. The LPF toxoid was sterile filtered through a 0.2 u membrane.

Example 8

This Example illustrates the detoxification of FHA with formaldehyde.

The purified FHA, prepared as described in Example 6, in 200 mM potassium phosphate at pH 8.0 containing 0.6M potassium chloride was diluted with glycerol to give a final concentration of 25% V/V. The protein concentrations was approximately 500 μg/ml based on the Lowry protein assay. The FHA solution was heated to 37° C. and a 1.5M solution of L-lysine HCl at pH 8.0 was added to a final concentration of 50 mM. Formaldehyde was added to a final concentration of 0.25% V/V. Detoxification was carried out at 37° C. for a period of 6 weeks. The resulting toxoid was diafiltered against 10 volumes of 10 mM potassium phosphate at pH 8.0 containing 0.5M sodium chloride to remove both the glycerol and the formaldehyde. The toxoid solution was sterile filtered through a 0.2 μ membrane.

Example 9

This Example illustrates the use of detoxified LPF and FHA in producing protective antibodies.

Guinea pigs (SPF) were prescreened for pertussis antibody titres, and only those animals which showed low background titres were used in the experiment.

Animals were injected with 0.5 ml of test material at day zero. Test materials employed in the tests were the purified and detoxified LPF and FHA products produced by the procedures of Examples 7 and 8 respectively ("adsorbed"), LPF and FHA isolated from broth but not processed by the invention ("unadsorbed") and conventional whole cell vaccine.

Four weeks after injection, the animals were bled and the sera tested for PT and FHA antibodies by ELISA. Sera also were tested for CHO antitoxin activity. At day 35, the animals were boosted with the same dose of antigen and finally the animals were bled at day 49 and the sera tested. The results are shown in the following Table I:

TABLE I

| | IMMUNOGENICITY OF PERTUSSIS TOXOID In guinea pigs at 25 ug dose | | | | | | |
|---|---|---|---|---|---|---|---|
| | | | | ELISA × $10^{-3}$ | | | |
| | Protein ug | CHO Units | | LPF | | FHA | |
| | | 1st | 2nd | 1st bleed | 2nd bleed | 1st bleed | 2nd bleed |
| LPF (unadsorbed) | 25 | 14 | 640 | 3 | 256 | | |
| (adsorbed) | 25 | 433 | 1664 | 59 | 410 | | |
| FHA (unadsorbed) | 25 | | | | | 52 | 33 |
| (adsorbed) | 25 | | | | | 14 | 205 |
| Whole Cell (unadsorbed) | human dose | 4 | 30 | 2 | 21 | 4 | 21 |

All results are reciprocal reactive titres.

The results set forth in the Table indicate that when compared to the conventional whole cell vaccine and unprocessed LPF and FHA proteins, the purified and detoxified LPF and FHA proteins provided by the procedures of the invention give considerably higher antibody titres.

Example 10

This Example illustrates the use of the purified antigens in the mouse protection test.

Taconic mice (15 to 17g) were injected at day zero with 0.5 ml of the test sample intraperitoneally, in three doses. Each dose was injected into 16 mice. At day 14, the mice were challenged with an intracerebral injection of a standard does of B.pertussis. Control mice also were injected at the same time to ascertain the effectiveness of the challenge. Three days after the challenge, the number of animal deaths was recorded every day up to and including day 28. At day 28, paralysed mice and mice with cerebral edema also were recorded as dead.

Results were recorded as $ED_{50}$, which is the dose at which half the mice survive the challenge. This was done using a computer programme after plotting the survivors divided by the total number of mice in each category at each dose.

The result of this experiment showed that the $ED_{50}$ of a mixture of LPF and FHA was less than [lug LPF+2 ug FHA], and thus a mixture of the two purified proteins was protective against the disease.

SUMMARY OF DISCLOSURE

In summary of this disclosure, the present invention provides a novel and unexpected method for the separation of proteins from the growth media of *B.pertussis* that can be used as antigens to elicit protection against the disease of pertussis. The novel method employs a difference in ionic strengths of the solutions from which the proteins are adsorbed and the solutions used to desorb them from the substrate. A further aspect of the invention is the reduction of LPS by washing the adsorbed proteins with a solution of detergent. The use of glycerol or sucrose for preventing protein aggregation during the detoxification process, is an important aspect of the invention since protein aggregation could result in up to 95% of protein losses at the final step of the process. Modifications are possible within the scope of this invention.

What we claim is:

1. A method for the isolation and purification of the proteinaceous materials called lymphocytosis promoting factor (LPF) and filamentous hemaglutinin (FHA) from a growth medium in which has been grown the *Bordatella pertussis* organism, which comprises:

contacting said growth medium at an ionic strength corresponding to a conductivity of about 11 mS/cm or less with a solid particulate adsorbing medium to selectively adsorbing LPF and FHA from the growth medium, and sequentially or simultaneously desorbing the selectively adsorbed proteinaceous materials by contacting said adsorbing medium with an aqueous medium of ionic strength corresponding to a conductivity of greater than about 11 mS/cm and sufficient to effect said desorption.

2. The method of claim 1 wherein said adsorbing medium is selected from the group consisting of filter aids, siliceous materials, celluloses, agaroses and gel filtration media.

3. The method of claim 1, wherein said adsorbing medium is selected from Perlite and Celite.

4. The method of claim 1, wherein said growth medium has an ionic strength of about 4 mS/cm or less when contacting said adsorbing medium to effect said selected adsorption.

5. The method of claim 4, wherein said aqueous medium has an ionic strength of at least about 50 mS/cm when contacting said adsorbing medium to effect said desorption.

6. The method of claim 1, wherein said FHA and LPF are desorbed from said adsorbing medium simultaneously.

7. The method of claim 6, wherein said simultaneously desorbed LPF and FHA are subsequently separated one from another.

8. The method of claim 1, wherein said adsorbing medium first is contacted with an aqueous medium having an ionic strength sufficient to selectively desorb LPF in preference to said FHA and then is contacted with an aqueous medium having an ionic strength sufficient to desorb FHA.

9. The method of claim 8, wherein said first-mentioned aqueous medium has an ionic strength from about 11 mS/cm to about 20 mS/cm and said second-mentioned aqueous medium has an ionic strength of at least about 20 mS/cm.

10. The method of claim 1, wherein, subsequent to said adsorption step and prior to said desorption step, said adsorbing medium is contacted with an aqueous non-ionic detergent solution selective to elute lipopolysaccharides (LPS) from the adsorbing medium in preference to said LPF and FHA.

11. The method of claim 10, wherein said non-ionic detergent solution is effective to decrease the LPS contamination of said LPF and FHA after said desorbtion to about 1 to about 10 ng/ml.

12. The method of claim 11 wherein said non-ionic detergent is selected from Triton X-100 of concentration of 0.005 to about 5% (v/v) and Nonidet p40 in a concentration of about 0.0005 to about 0.1% (v/v).

13. The method of claim 11, wherein, subsequent to desorption of said LPF and FHA, the purified proteinaceous material is detoxified by contact with a cross-linking agent in the presence of an anti-aggregation agent.

14. The method of claim 13, wherein said cross-linking agent is selected from glutaraldehyde, formaldehyde and mixtures thereof and said anti-aggregation agent is selected from sucrose, glycerol and mixtures thereof.

15. The method of claim 13 wherein, subsequent to desorption of said LPF and FHA and prior to said detoxification, said LPF and FHA are subjected to further purification on hydroxyapatite.

16. The method of claim 15, including the subsequent steps of sterilizing the proteins and formulating them as a vaccine against pertussis.

17. The method of claim 1 wherein:

said growth medium has an ionic strength corresponding to a conductivity of 4mS or less and is contacted with Perlite as said adsorbing medium to provide an adsorbed protein loading of about 1 to about 5 mg per milliliter of Perlite, said Perlite is provided in the form of a packed column having a height of about 15 to about 18 cm and a diameter of about 10 to about 45 cm and said growth medium is contacted with said Perlite at a linear flow rate of about 50 to about 200 cm/hr., said column having adsorbed LPF and FHA is washed with about 2 to about 10 column volumes of a buffer containing about 10 to about 50 mM Tris HCl at pH 8.0, then is washed with an aqueous non-ionic detergent solution to remove lipopolysaccharides (LPS) from the column and to provide an overall decrease in the LPS/LPF weight ratio between that in said growth medium and that in eluted LPF of between about 10,000 and about 100,000, and subsequently is washed further with said buffer to remove said non-ionic detergent from said column and to provide a washed column, and LPF is eluted from the column by contacting said washed column with an aqueous eluting medium containing about 0.1 to about 0.2 mM sodium chloride therein and said FHA is subsequently eluted from the column by contacting said washed column with an aqueous eluting medium containing at least 0.2M sodium chloride therein.

18. The method of claim 17 wherein the eluate containing LPF is further purified by:

contacting a column of hydroxyapatite having a diameter of about 5 to about 30 cm and a height of about 5 to about 8 cm with said eluate at a loading of about 0.5 to about 1 mg of protein/ml of hydroxyapatite at a linear flow rate of about 15 to about 25 cm/hr to adsorb said LPF thereon, and subsequently eluting the LPF from said hydroxyapatite using an aqueous eluant medium containing about 0.1 to about 0.3M sodium chloride.

19. The method of claim 17 wherein the eluate containing FHA is further purified by:

contacting a column of hydroxyapatite having a diameter of about 5 to about 30 cm and a height of about 5 to about 8 cm with said eluate at a loading of about 0.5 to about 1 mg of protein/ml of hydroxyapatite at a linear flow rate of about 15 to about 25 cm/hr to adsorb said LPF thereon, and subsequently eluting the FHA from said hydroxyapatite using an aqueous eluant medium containing at least about 0.2M sodium chloride.

* * * * *